US 8,994,804 B2

(12) United States Patent
Hirakawa et al.

(10) Patent No.: US 8,994,804 B2
(45) Date of Patent: Mar. 31, 2015

(54) SCANNING ENDOSCOPE SYSTEM

(71) Applicant: Olympus Medical Systems Corp., Tokyo (JP)

(72) Inventors: Katsumi Hirakawa, Sagamihara (JP); Masahiro Yoshino, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/195,263

(22) Filed: Mar. 3, 2014

(65) Prior Publication Data

US 2014/0210975 A1 Jul. 31, 2014

Related U.S. Application Data

(63) Continuation of application No. PCT/JP2013/062916, filed on May 8, 2013.

(30) Foreign Application Priority Data

Sep. 3, 2012 (JP) .................................. 2012-193339

(51) Int. Cl.
| | |
|---|---|
| A61B 1/00 | (2006.01) |
| G02B 23/26 | (2006.01) |
| A61B 1/04 | (2006.01) |
| A61B 1/07 | (2006.01) |
| G02B 23/24 | (2006.01) |
| G02B 26/10 | (2006.01) |

(52) U.S. Cl.
CPC .............. *A61B 1/00172* (2013.01); *A61B 1/04* (2013.01); *A61B 1/07* (2013.01); *G02B 23/26* (2013.01); *G02B 23/2423* (2013.01); *G02B 26/101* (2013.01)

USPC .......................................... 348/68; 348/220.1

(58) Field of Classification Search
None
See application file for complete search history.

(56) References Cited

U.S. PATENT DOCUMENTS

| 7,554,572 B2* | 6/2009 | Takahashi ........................ 348/65 |
|---|---|---|
| 2006/0072843 A1* | 4/2006 | Johnston ........................ 382/254 |
| 2008/0221388 A1* | 9/2008 | Seibel et al. ................... 600/109 |

(Continued)

FOREIGN PATENT DOCUMENTS

| JP | 2005-021651 A | 1/2005 |
|---|---|---|
| JP | 2006-314808 A | 11/2006 |

(Continued)

*Primary Examiner* — Jay Patel
*Assistant Examiner* — Reza Aghevli
(74) *Attorney, Agent, or Firm* — Scully, Scott, Murphy & Presser, PC

(57) ABSTRACT

A scanning endoscope system includes: a scanning endoscope including a light-guiding section that guides illumination light, a driving section that causes the light-guiding section to swing such that an irradiation position of the illumination light draws a trajectory corresponding to a predetermined scanning pattern; and a light-receiving section that receives return light of the illumination light; a test chart device including a plane portion having first and second regions; a light detection section that outputs a signal corresponding to an intensity of the return light; a pixel generation section that generates pixels on the predetermined scanning pattern; a first correction value calculation section that calculates a correction value based on a pixel value of each of the pixels in the first region; and a second correction value calculation section that calculates a correction based on a pixel position of each of the pixels in the second region.

7 Claims, 7 Drawing Sheets

(56) References Cited

U.S. PATENT DOCUMENTS

| | | | |
|---|---|---|---|
| 2009/0028407 A1* | 1/2009 | Seibel et al. | 382/131 |
| 2009/0231983 A1* | 9/2009 | Takahashi | 369/112.04 |
| 2010/0284045 A1* | 11/2010 | Kawano et al. | 358/474 |
| 2011/0263955 A1* | 10/2011 | Narita et al. | 600/341 |

FOREIGN PATENT DOCUMENTS

| | | |
|---|---|---|
| JP | 2008-514342 A | 5/2008 |
| WO | WO 2006/041452 A1 | 4/2006 |
| WO | WO 2008/085186 A1 | 7/2008 |

\* cited by examiner

SCANNING ENDOSCOPE SYSTEM

CROSS REFERENCE TO RELATED APPLICATION

This application is a continuation application of PCT/JP2013/062916 filed on May 8, 2013 and claims benefit of Japanese Application No. 2012-193339 filed in Japan on Sep. 3, 2012, the entire contents of which are incorporated herein by this reference.

BACKGROUND OF THE INVENTION

1. Field of the Invention

The present invention relates to a scanning endoscope system, and more particularly to a scanning endoscope system that acquires an image by scanning an object.

2. Description of the Related Art

Various kinds of techniques for reducing a size of an insertion portion to be inserted into a body cavity of a subject are proposed for endoscopes in the medical fields, in order to alleviate a burden on the subject. As one example of such techniques, a scanning endoscope which does not include a solid-state image pickup device at the part corresponding to the above-described insertion portion, and a system provided with the scanning endoscope are known.

Specifically, the system including the above-described scanning endoscope is configured, for example, to scan an object in a preset scanning pattern by causing the distal end portion of the illumination fibers for guiding illumination light emitted from the light source section to swing, receive return light from the object with the light-receiving fibers arranged around the illumination fibers, and generate an image of the object using a signal obtained by separating the return light received with the light-receiving fibers into color components.

As a calibration method applicable to the system including the above-described configuration, the calibration method disclosed in Japanese Unexamined Patent Application Publication No. 2010-515947 has been conventionally known, for example. Specifically, Japanese Unexamined Patent Application Publication No. 2010-515947 discloses the calibration method of acquiring a multi-colored image in the multi-colored calibration pattern using a scanning beam device, comparing the respective color components of the acquired multi-colored image with the display color components of the multi-colored calibration pattern, which correspond to the respective color components, and calibrates the scanning beam device based on the result of the comparison.

In addition, in a common image pickup apparatus and the like, a color balance adjustment has been conventionally performed for bringing the color of the object included in an image close to the natural color when the object is seen with the naked eye, for example.

SUMMARY OF THE INVENTION

A scanning endoscope system according to one aspect of the present invention includes: a scanning endoscope including a light-guiding section that guides illumination light emitted from a light source, a driving section that enables the light-guiding section to swing such that an irradiation position of the illumination light emitted to an object through the light-guiding section draws a trajectory corresponding to a predetermined scanning pattern, and a light-receiving section that receives return light of the illumination light emitted to the object; a test chart device comprising a plane portion including a first region and a second region; a light detection section configured to generate a signal corresponding to an intensity of the return light received at the light-receiving section and output the generated signal; a pixel generation section configured to generate sampling pixels on the predetermined scanning pattern by sampling the signal outputted from the light detection section in a given sampling cycle; a first correction value calculation section configured to extract the first region from an image of the plane portion which includes the respective sampling pixels generated by the pixel generation section, and to further calculate a first correction value to be used for color balance adjustment of an image of the object based on a pixel value of each of the sampling pixels included in the first region; and a second correction value calculation section configured to extract the second region from the image of the plane portion which includes the respective sampling pixels generated by the pixel generation section, and to further calculate a second correction value to be used for pixel shift correction of the image of the object based on a pixel position of each of the sampling pixels included in the second region.

DETAILED DESCRIPTION OF THE PREFERRED EMBODIMENT

Hereinafter, an embodiment of the present invention will be described with reference to drawings.

Figure 1:
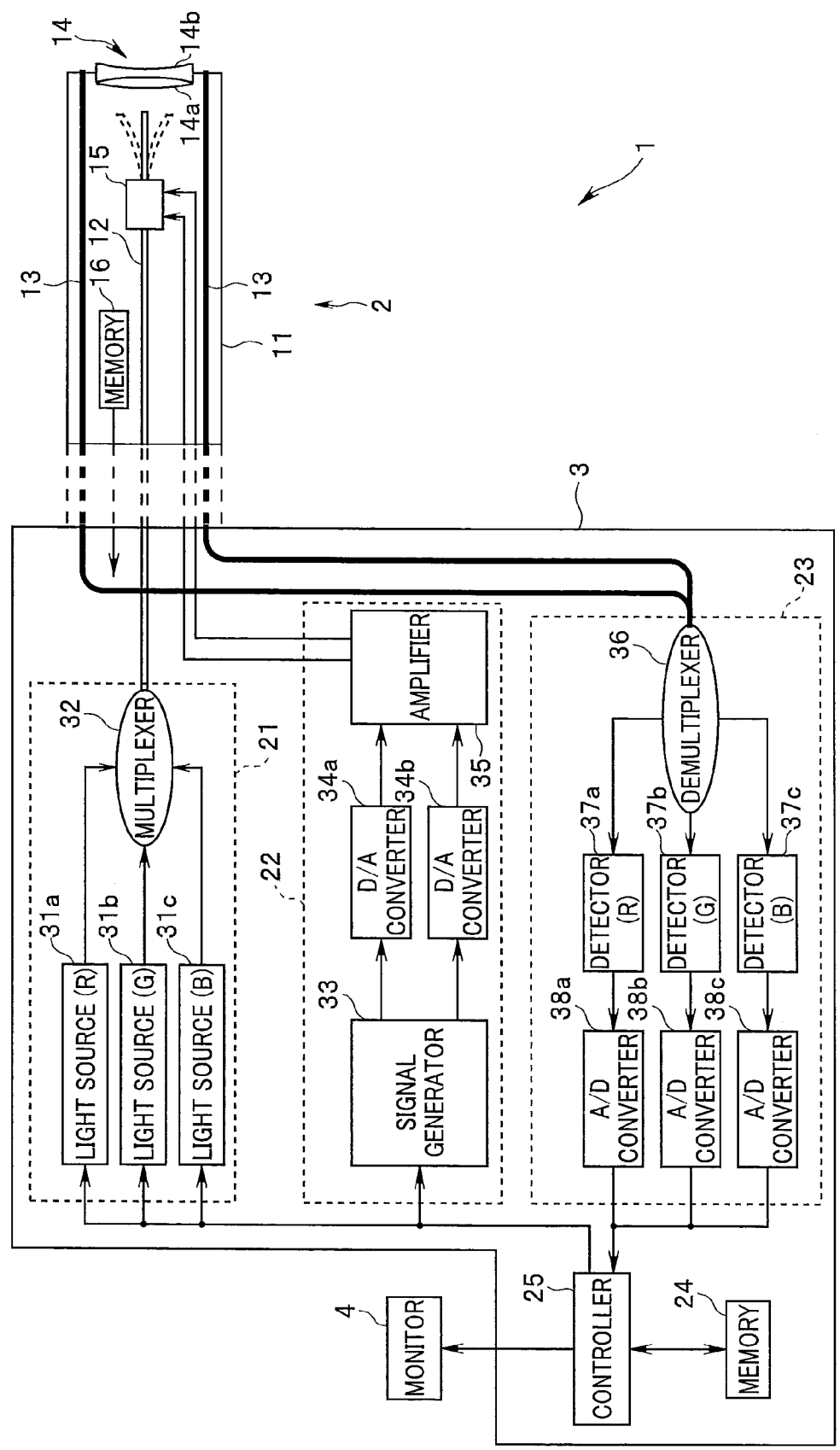
FIG. 1 illustrates a configuration of a main part of a scanning endoscope system according to an embodiment.

FIGS. 1 to 9 relate to the embodiment of the present invention. FIG. 1 illustrates a configuration of a main part of a scanning endoscope system according to the embodiment.

A scanning endoscope system 1 includes a scanning endoscope 2 to be inserted into a body cavity of a subject, a main body apparatus 3 connected to the scanning endoscope 2, and a monitor 4 connected to the main body apparatus 3, as shown in FIG. 1, for example.

The scanning endoscope 2 includes an insertion portion 11 formed in an elongated shape and having flexibility so as to be insertable into the body cavity of the subject. The insertion portion 11 includes at the proximal end portion thereof a connector and the like, not shown, for detachably connecting the scanning endoscope 2 to the main body apparatus 3.

Illumination fibers 12 having a function as a light-guiding section that guides the illumination light supplied from a light source unit 21 of the main body apparatus 3 to an objective optical system 14 and light-receiving fibers 13 that receive return light from the object to guide the received light to a detection unit 23 of the main body apparatus 3 are respectively inserted through a part from the proximal end portion to the distal end portion inside the insertion portion 11.

An end portion including a light incident surface of the illumination fibers 12 is arranged at a multiplexer 32 provided in the main body apparatus 3. In addition, an end portion including a light exit surface of the illumination fibers 12 is arranged in the vicinity of a light incident surface of a lens 14a provided at the distal end portion of the insertion portion 11 in a state where the end portion is not fixed with a fixing member or the like.

An end portion including a light incident surface of the light-receiving fibers 13 is fixedly arranged around the light exit surface of the lens 14b on the distal end surface of the distal end portion of the insertion portion 11. In addition, an end portion including the light exit surface of the light-receiving fibers 13 is arranged at a demultiplexer 36 provided in the main body apparatus 3.

The objective optical system 14 includes the lens 14a on which the illumination light from the illumination fibers 12 is incident, and a lens 14b that emits the illumination light passed through the lens 14a to the object.

At the halfway portion of the illumination fibers 12, which is located on the distal end portion side of the insertion portion 11, an actuator 15 that drives based on a driving signal outputted from a driver unit 22 of the main body apparatus 3 is attached.

Figure 2:
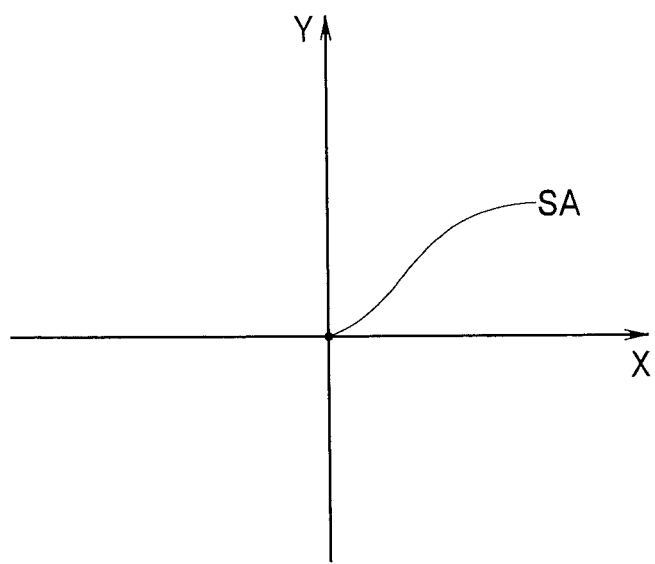
FIG. 2 illustrates an example of a virtual XY plane set on a surface of an object.

Hereinafter, description will be made by taking the case where the XY plane as shown in FIG. 2 is set on the surface of the object as a virtual plane perpendicular to the insertion axis (or the optical axis of the objective optical system 14) corresponding to the axis in the longitudinal direction of the insertion portion 11, as an example. FIG. 2 illustrates an example of the virtual XY plane set on the surface of the object.

Specifically, the point SA on the XY plane in FIG. 2 shows an intersection of the insertion axis and the paper surface based on a virtual setting in which the insertion axis of the insertion portion 11 is supposed to exist in the direction from the near side to the far side of the paper surface. The X-axis direction on the XY plane in FIG. 2 is set as the direction from the left side toward the right side of the paper surface. The Y-axis direction on the XY plane in FIG. 2 is set as the direction from the down side toward the up side of the paper surface. The X-axis and the Y-axis which constitute the XY plane in FIG. 2 intersect with each other at the point SA.

The actuator 15 includes an X-axis actuator (not shown) that operates so as to cause the end portion including the light exit surface of the illumination fibers 12 to swing in the X-axis direction on the basis of a first driving signal outputted from the driver unit 22 of the main body apparatus 3, and the Y-axis actuator (not shown) that operates so as to cause the end portion including the light exit surface of the illumination fibers 12 to swing in the Y-axis direction on the basis of a second driving signal outputted from the driver unit 22 of the main body apparatus 3. The end portion including the light exit surface of the illumination fibers 12 is spirally swung with the point SA as the center in accordance with the operations of the X-axis actuator and the Y-axis actuator as described above.

The insertion portion 11 includes inside thereof a memory 16 in which endoscope information including various kinds of information such as individual discrimination information of the scanning endoscope 2 are stored in advance. The endoscope information stored in the memory 16 is read by the controller 25 when the scanning endoscope 2 is connected to the main body apparatus 3.

On the other hand, the main body apparatus 3 includes the light source unit 21, the driver unit 22, the detection unit 23, a memory 24, and the controller 25.

The light source unit 21 includes light sources 31a, 31b, and 31c, and the multiplexer 32.

The light source 31a includes a laser light source, or the like, for example, and emits light in a red wavelength band (hereinafter, referred also as R light) to the multiplexer 32 when being turned on under the control by the controller 25.

The light source 31b includes a laser light source, or the like, for example, and emits light in a green wavelength band (hereinafter also referred to as G light) to the multiplexer 32 when being turned on under the control by the controller 25.

The light source 31c includes a laser light source, or the like, for example, and emits light in a blue wavelength band (hereinafter also referred to as B light) to the multiplexer 32 when being turned on under the control by the controller 25.

The multiplexer 32 is configured to be able to multiplex the R light emitted from the light source 31a, the G light emitted from the light source 31b, and the B light emitted from the light source 31c, to supply the multiplexed light to the light incident surface of the illumination fibers 12.

The driver unit 22 includes a signal generator 33, digital/analog (hereinafter referred to as D/A) converters 34a, 34b, and an amplifier 35.

Figure 3:
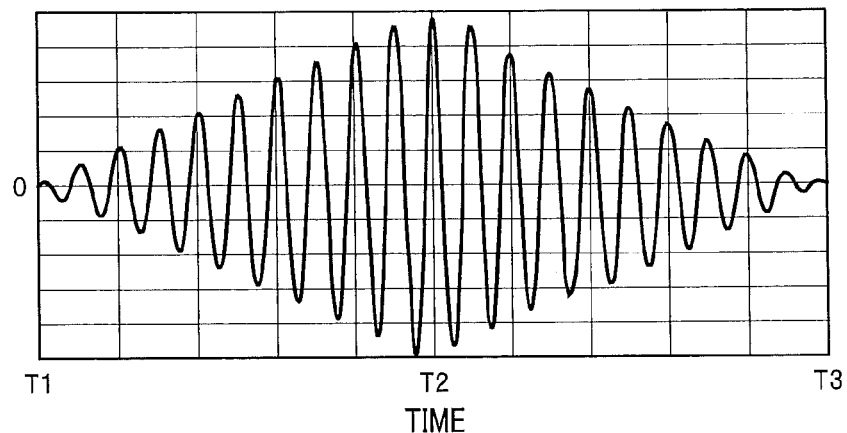
FIG. 3 illustrates an example of a signal waveform of a first driving signal supplied to an actuator provided in an endoscope.

The signal generator 33 generates a signal of a predetermined waveform as shown in FIG. 3, for example, as the first driving signal for causing the end portion including the light exit surface of the illumination fibers 12 to swing in the X-axis direction, to output the generated signal to the D/A converter 34a, based on the control by the controller 25. FIG. 3 illustrates an example of the signal waveform of the first driving signal supplied to the actuator provided in the scanning endoscope.

Figure 4:
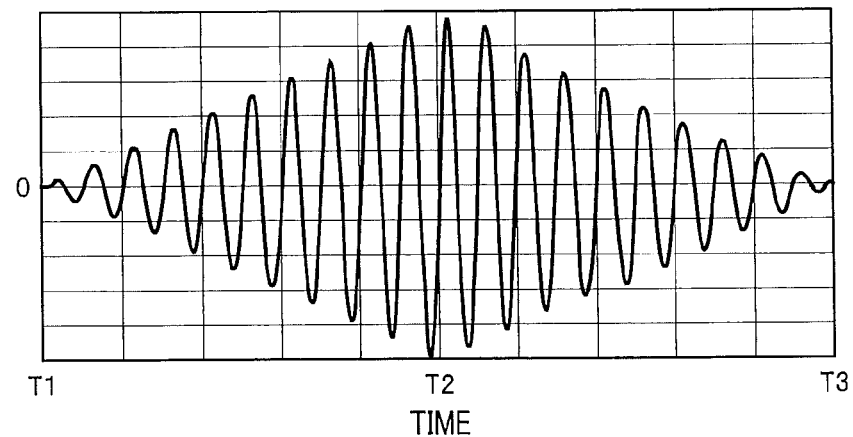
FIG. 4 illustrates an example of a signal waveform of a second driving signal supplied to the actuator provided in the endoscope.

In addition, the signal generator 33 generates a signal of a waveform whose phase is shifted by 90 degrees from the phase of the waveform of the above-described first driving signal, as shown in FIG. 4, for example, as the second driving signal for causing the end portion including the light exit surface of the illumination fibers 12 to swing in the Y-axis direction, to output the generated signal to the D/A converter 34b, based on the control by the controller 25. FIG. 4 illustrates an example of the signal waveform of the second driving signal supplied to the actuator provided in the scanning endoscope.

The D/A converter 34a converts the first driving signal in the digital form outputted from the signal generator 33 into the first driving signal in the analog form, to output the converted driving signal to the amplifier 35.

The D/A converter 34b converts the second driving signal in the digital form outputted from the signal generator 33 into the second driving signal in the analog form, to output the converted signal to the amplifier 35.

The amplifier 35 amplifies the first and second driving signals respectively outputted from the D/A converters 34a and 34b, to output the amplified driving signals to the actuator 15.

The amplitude value (signal level) of the first driving signal exemplified in FIG. 3 gradually increases with the time T1 at which the amplitude value is minimum value, as a starting point, then gradually decreases after reaching the maximum value at the time T2, and becomes the minimum value again at the time T3.

In addition, the amplitude value (signal level) of the second driving signal exemplified in FIG. 4 gradually increases at the time T1 at which the amplitude value is minimum value, as a starting point, then gradually decreases after reaching the maximum value around the time T2, and becomes the minimum value again at the time T3.

Figure 5A:
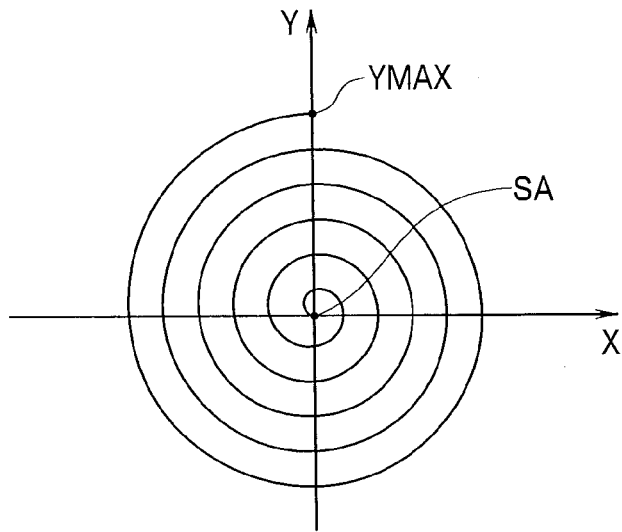
FIG. 5A illustrates a temporal displacement of an irradiation coordinate of illumination light from a point SA to reach a point YMAX in the case where the virtual XY plane as shown in FIG. 2 is irradiated with the illumination light.
Figure 5B:
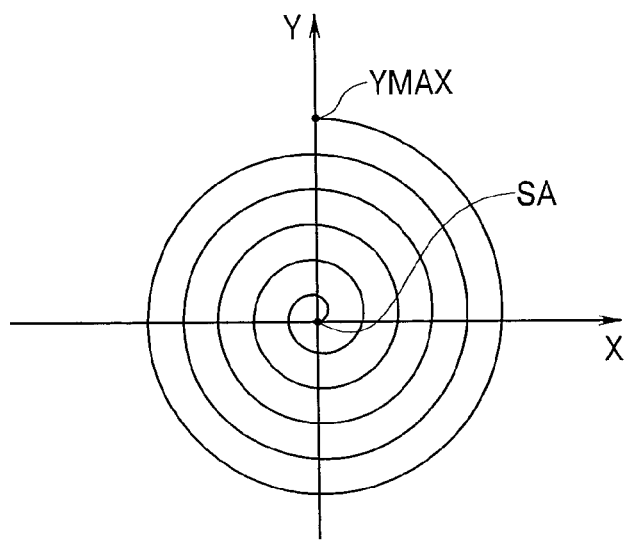
FIG. 5B illustrates a temporal displacement of the irradiation coordinate of illumination light from the point YMAX to reach the point SA in the case where the virtual XY plane as shown in FIG. 2 is irradiated with the illumination light.

When the first driving signal as shown in FIG. 3 is supplied to the X-axis actuator of the actuator 15 and the second driving signal as shown in FIG. 4 is supplied to the Y-axis actuator of the actuator 15, the end portion including the light exit surface of the illumination fibers 12 is swung in a spiral shape with the point SA as the center, and in accordance with such a swing, the surface of the object is scanned in the spiral shapes as shown in FIGS. 5A and 5B. FIG. 5A illustrates a temporal displacement of an irradiation coordinate of the illumination light from the point SA to reach the point YMAX in the case where the virtual XY plane as shown in FIG. 2 is irradiated with the illumination light. FIG. 5B illustrates a temporal displacement of the irradiation coordinate of the illumination light from the point YMAX to reach the point SA in the case where the virtual XY plane as shown in FIG. 2 is irradiated with the illumination light.

Specifically, the position corresponding to the point SA on the surface of the object is irradiated with the illumination light at the time T1. After that, in accordance with the increase in the amplitude values of the first and second driving signals from the time T1 to the time T2, the irradiation coordinate of the illumination light on the surface of the object displaces so as to draw a first spiral-shaped trajectory toward outside with the point SA as the starting point, and when the time reaches the time T2, the point YMAX, which is the outmost point of the irradiation coordinate of the illumination light on the surface of the object, is irradiated with the illumination light. Then, in accordance with the decrease in the amplitude values of the first and second driving signals from the time T2 to the time T3, the irradiation coordinate of the illumination light on the surface of the object displaces so as to draw a second spiral-shaped trajectory toward inside with the point YMAX as the starting point, and when the time reaches the time T3, the point SA on the surface of the object is irradiated with the illumination light.

That is, the actuator 15 is capable of causing the end portion including the light exit surface of the illumination fibers 12 to swing such that the irradiation position of the illumination light emitted through the objective optical system 14 to the object draws the trajectory corresponding to each of the spiral-shaped scanning patterns as illustrated in FIG. 5A and FIG. 5B, based on the first and second driving signals supplied from the driver unit 22.

The detection unit 23 includes the demultiplexer 36, the detectors 37a, 37b, and 37c, and analog/digital (hereinafter referred to as A/D) converters 38a, 38b, and 38c.

The demultiplexer 36 includes a dichroic mirror, etc., and separates the return light emitted from the light exit surface of the light-receiving fibers 13 into light of each of the color components of R (red), G (green), and B (blue), to emit the light subjected to the separation to the detectors 37a, 37b, and 37c.

The detector 37a detects the intensity of the R light outputted from the demultiplexer 36 and generates an analog R signal corresponding to the detected intensity of the R light, to output the generated analog R signal to the A/D converter 38a.

The detector 37b detects the intensity of the G light outputted from the demultiplexer 36, and generates an analog G signal corresponding to the detected intensity of the G light, to output the generated analog G signal to the A/D converter 38b.

The detector 37c detects the intensity of the B light outputted from the demultiplexer 36, and generates an analog B signal corresponding to the detected intensity of the B light, to output the generated analog B signal to the A/D converter 38c.

The A/D converter 38a converts the analog R signal outputted from the detector 37a into a digital R signal, to output the digital R signal to the controller 25.

The A/D converter 38b converts the analog G signal outputted from the detector 37b into a digital G signal, to output the digital G signal to the controller 25.

The A/D converter 38c converts the analog B signal outputted from the detector 37c into a digital B signal, to output the digital B signal to the controller 25.

The memory 24 stores, in advance, a control program for controlling the main body apparatus 3 and the like. In addition, the memory 24 stores a mapping table MPT1 including information related to the coordinate position (pixel position) of each of sampling pixels sampled in a given sampling cycle SC when the illumination light is emitted (in a period corresponding to the time T1 to the time T2) along the scanning pattern in the ideal spiral shape as shown in FIG. 5A, and a mapping table MPT2 including information related to the coordinate position (pixel position) of each of sampling pixels sampled in the given sampling cycle SC when the illumination light is emitted (in a period corresponding to the time T2 to the time T3) along the scanning pattern in the ideal spiral shape as shown in FIG. 5B.

The controller 25 includes a CPU, etc., and is configured to read the control program stored in the memory 24 and control the light source unit 21 and the driver unit 22 based on the read control program.

In a case where the controller 25 detects that the endoscope information read from the memory 16 when the insertion portion 11 is connected to the main body apparatus 3 is not stored (saved) in the memory 24, the controller 25 stores (saves) the read endoscope information into the memory 24.

The controller 25 acquires a white balance correction value to be used in white balance adjustment processing, based on the R signal, the G signal, and the B signal outputted from the detection unit 23 in accordance with the return light received when a bottom surface portion 102 of a test chart device 101 to be described later is irradiated with the illumination light, to store the acquired white balance correction value into the memory 24.

The controller 25 acquires a pixel shift correction value to be used in pixel shift correction processing, based on the R signal, the G signal, and the B signal outputted from the detection unit 23 in accordance with the return light received when the bottom surface portion 102 of the test chart device 101 to be described later is irradiated with the illumination light, to write the acquired pixel shift correction value into the mapping table MPT1 or MPT2 in the memory 24.

The controller 25 includes a function as a pixel generation section and is capable of generating sampling pixels by sampling the R signal, the G signal, and the B signal outputted from the detection unit 23 in the given sampling cycle SC in a period corresponding to the time T1 to the time T2, generating interpolation pixels by performing interpolation processing based on the sampling pixels, and further generating an image for one frame based on the sampling pixels and the interpolation pixels. In addition, the controller 25 is capable of respectively performing the white balance adjustment processing based on white balance correction values stored in the memory 24 and the pixel shift correction processing based on pixel shift correction values written into the mapping table MPT1 stored in the memory 24, on the image for one frame (in the period corresponding to the time T1 to the time T2) generated as described above.

The controller 25 includes the function as the pixel generation section and is capable of generating sampling pixels by sampling the R signal, the G signal, and the B signal outputted from the detection unit 23 in the given sampling cycle SC in a period corresponding to the time T2 to the time T3, generating interpolation pixels by performing interpolation processing based on the sampling pixels, and further generating an image for one frame based on the sampling pixels and the interpolation pixels. In addition, the controller 25 is capable of respectively performing the white balance adjustment processing based on white balance correction values stored in the memory 24 and the pixel shift correction processing based on pixel shift correction values written into the mapping table MPT2 stored in the memory 24, on the image for one frame (in the period corresponding to the time T2 to the time T3) generated as described above.

The controller 25 causes the image subjected to the white balance adjustment processing and the pixel shift correction processing to be displayed on the monitor 4.

Figure 6:
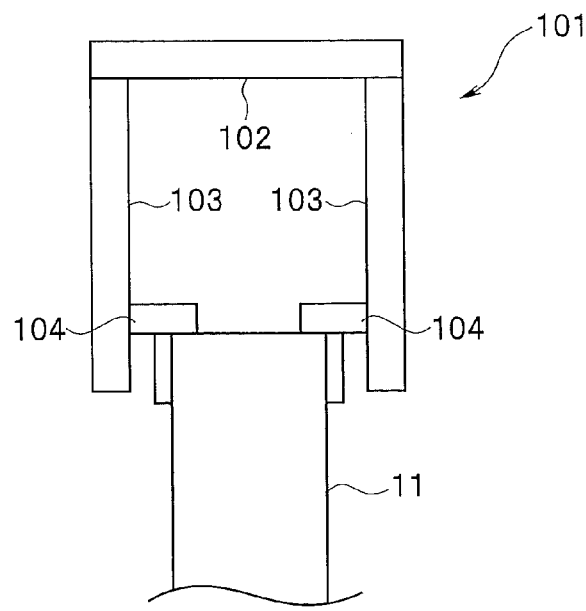
FIG. 6 illustrates a configuration of a test chart device used together with the scanning endoscope system according to the embodiment.
Figure 7:
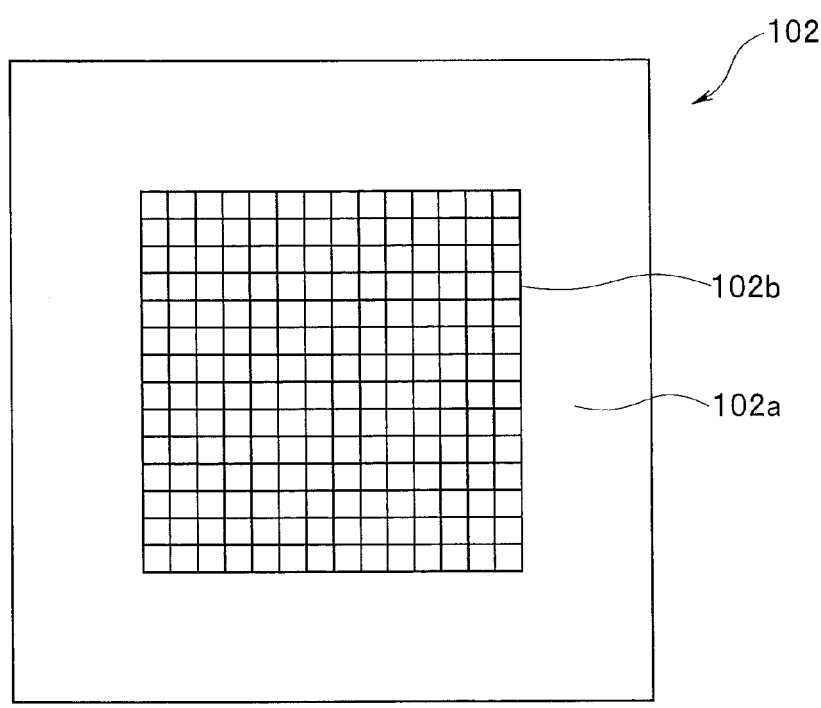
FIG. 7 illustrates an example of a configuration of a bottom surface portion of the test chart device.

Description will be made on the configuration of the test chart device 101 used for acquiring the above-described white balance correction values and the pixel shift correction values. FIG. 6 illustrates the configuration of the test chart device used together with the scanning endoscope system according to the embodiment. FIG. 7 illustrates an example of the configuration of the bottom surface portion of the test chart device.

As shown in FIG. 6, the test chart device 101 is formed as a bottomed cylinder body that allows the distal end portion of the insertion portion 11 to be inserted from an opening portion into an internal space of the cylinder body. In addition, as shown in FIGS. 6 and 7, the test chart device 101 has the bottom surface portion 102 as a plane portion provided inside the bottomed cylinder body, a white inner circumferential side surface portion 103, and a positioning member 104. The bottom surface portion 102 includes a region for white balance adjustment 102a and a region for pixel shift correction 102b.

The region for white balance adjustment 102a is configured as a solid white region provided at a peripheral portion of the bottom surface portion 102.

The region for pixel shift correction 102b is configured as a region with a lattice pattern which is provided (drawn) at the center of the bottom surface portion 102.

The respective segments in a vertical direction (corresponding to the Y-axis direction on the virtual XY plane shown in FIG. 2) included in the lattice pattern of the region for pixel shift correction 102b are drawn in a first color (red, for example) of red, green, and blue. The respective segments in a horizontal direction (corresponding to the X-axis direction on the virtual XY plane shown in FIG. 2) included in the lattice pattern of the region for pixel shift correction 102b, are drawn in a second color (green, for example) of red, green, and blue, which is different from the first color. Furthermore, the respective segments in the vertical direction and the horizontal direction included in the lattice pattern of the region for pixel shift correction 102b are drawn so as to be apart from each other by the fixed and the same space equal to or larger than the size of one pixel. The shape of the region for pixel shift correction 102b is not limited to the square shown in FIG. 2, but may be any shape of rectangle, circle, ellipse, and polygon, for example.

The positioning member 104 is formed as a cylindrical body (or tubular body) with a flange, as shown in FIG. 6, for example.

Specifically, the positioning member 104 has a shape that allows the distal end portion of the insertion potion 11 to be fixedly arranged at a position where the distal end surface of the insertion potion 11 and the bottom surface portion 102 face each other, with the distance between the distal end surface and the bottom surface portion 102 being maintained at a predetermined distance, when the insertion portion 11 is inserted into the internal space of the test chart device 101. Furthermore, the positioning member 104 includes a hole of such a diameter as not to shield the illumination light emitted through the objective optical system 14 in the state where the distal end portion of the insertion portion 11 is fixedly arranged at the above-described position.

Next, description will be made on the working, etc., of the scanning endoscope system 1 configured as described above. Hereinafter, description will be mainly made on the case where the endoscope information read from the memory 16 of the scanning endoscope 2 is not stored (saved) in the memory 24.

First, an operator or the like connects the scanning endoscope 2 and the monitor 4 respectively to the main body apparatus 3, and then inserts the scanning endoscope 2 from the opening portion into the internal space of the test chart device 101, to thereby arrange the distal end portion of the insertion portion 11 at the position where the distal end surface of the insertion portion 11 and the bottom surface portion 102 face each other, the distance between the distal end surface of the insertion portion 11 and the bottom surface portion 102 is maintained at a predetermined distance, and the optical axis of the objective optical system 14 coincides with the center of the lattice pattern of the region for pixel shift correction 102b. Such an arrangement allows the point SA on the virtual XY plane shown in FIG. 2 to coincide with the center of the lattice pattern of the region for pixel shift correction 102b.

When power sources of the respective sections in the scanning endoscope system 1 are turned on, the endoscope information stored in the memory 16 of the insertion portion 11 is read by the controller 25, and the read endoscope information is stored in the memory 24.

The controller 25 controls the light source unit 21 to switch the light sources 31a, 31b, and 31c from off to on and controls the driver unit 22 to cause the first and second driving signals to be outputted to the actuator 15, at a timing immediately after the endoscope information read from the memory 16 is stored in the memory 24. With such controls performed by the controller 25, the surface of the bottom surface portion 102 is irradiated with the white light obtained by mixing the R light, the G light, and the B light, which is the illumination light, the return light from the bottom surface portion 102 is received with the light-receiving fibers 13, and the R signal, the G signal, and the B signal corresponding to the return light received by the light-receiving fibers 13 are outputted from the detection unit 23.

After that, when the controller 25 detects that a calibration switch (not shown) provided on the main body apparatus 3 is pressed, for example, the controller 25 acquires the white balance correction values and the pixel shift correction values by performing the processing as described below.

Figure 8:
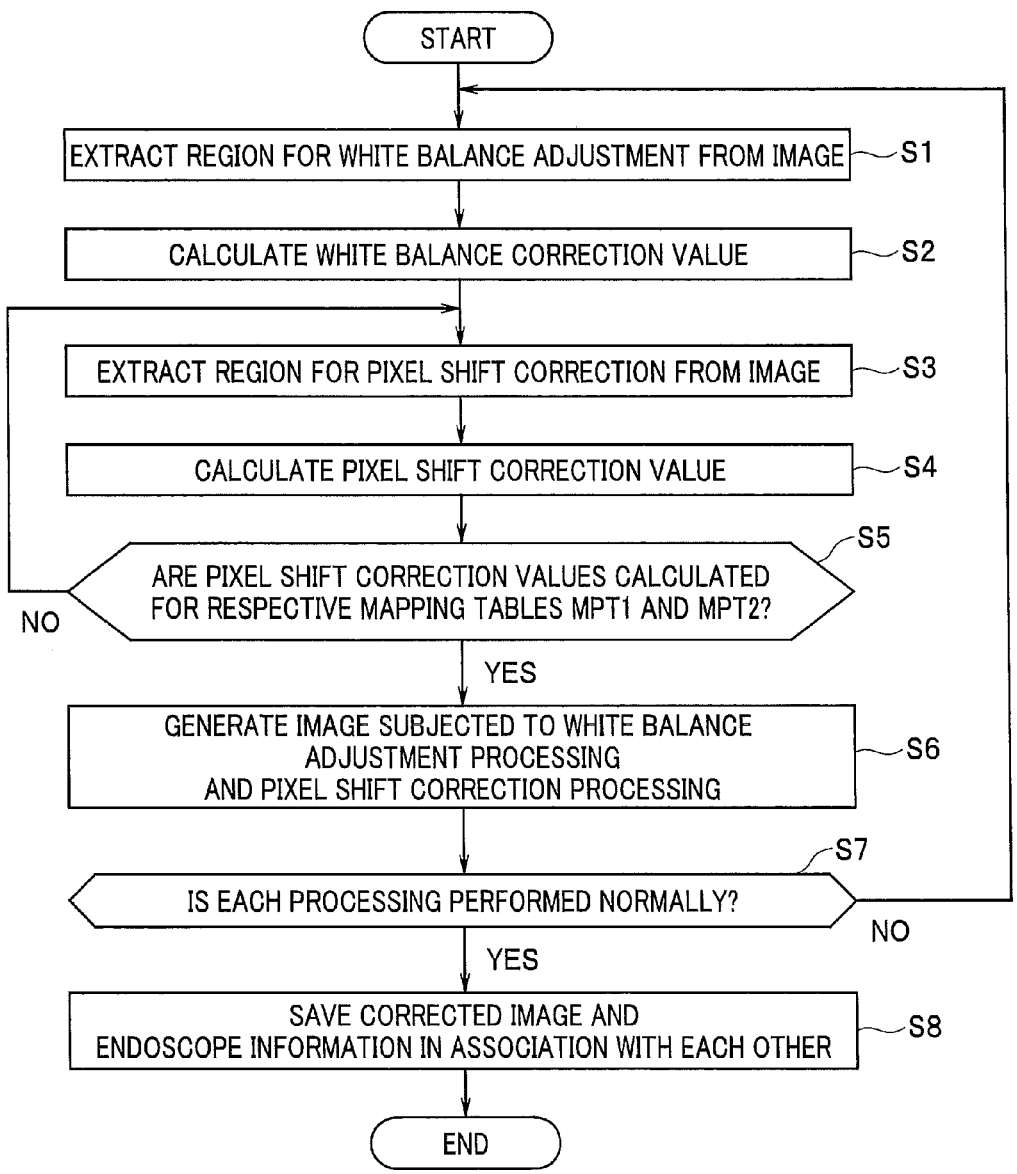
FIG. 8 is a flowchart showing an example of processing and the like performed in the scanning endoscope system according to the embodiment.

Now, description will be made on the processing related to the acquisition of the white balance correction values and the pixel shift correction values. FIG. 8 is a flowchart showing one example of processing and the like performed in the scanning endoscope system according to the embodiment.

The controller 25 generates the sampling pixels by sampling the R signal, the G signal, and the B signal outputted from the detection unit 23 in the given sampling cycle SC, generates the interpolation pixels by performing interpolation processing based on the sampling pixels, further generates an image of the bottom surface portion 102 based on the generated sampling pixels and interpolation pixels, and then extracts a region corresponding to the region for white balance adjustment 102a from the generated image of the bottom surface portion 102 (step S1 in FIG. 8).

The controller 25 calculates the white balance correction values based on the pixel values of the respective sampling pixels included in the region for white balance adjustment 102a extracted in the step S1 in FIG. 8 (step S2 in FIG. 8), and stores the calculated white balance correction values in the memory 24.

Specifically, the controller 25 respectively calculates an average value RPA of R-component pixel values, an average value GPA of G-component pixel values, and an average value BPA of B-component pixel values, for the respective sampling pixels included in the region for white balance adjustment 102a, for example, and then calculates the white balance correction values for setting the ratio of the calculated three average values RPA, GPA, and BPA as 1:1:1.

Then, the controller 25 extracts a region corresponding to the region for pixel shift correction 102b of the bottom surface portion 102 from the same image used for the extraction of the region for white balance adjustment 102a in the step S1 in FIG. 8 (step S3 in FIG. 8).

The controller 25 calculates the pixel shift correction values of the respective pixels included in the same image used for the extraction of the region for pixel shift correction 102b in the step S3 in FIG. 8 (step S4 in FIG. 8), and then writes the calculated pixel shift correction values of the respective pixels into the mapping table MPT1 or MPT2 in the memory 24.

Now, description will be made on one example of calculation performed when calculating the pixel shift correction values in the step S4 in FIG. 8. Hereinafter, for simplification, description will be made by taking the case where the pixel shift correction values in the vertical direction are calculated, as a main example.

Figure 9:
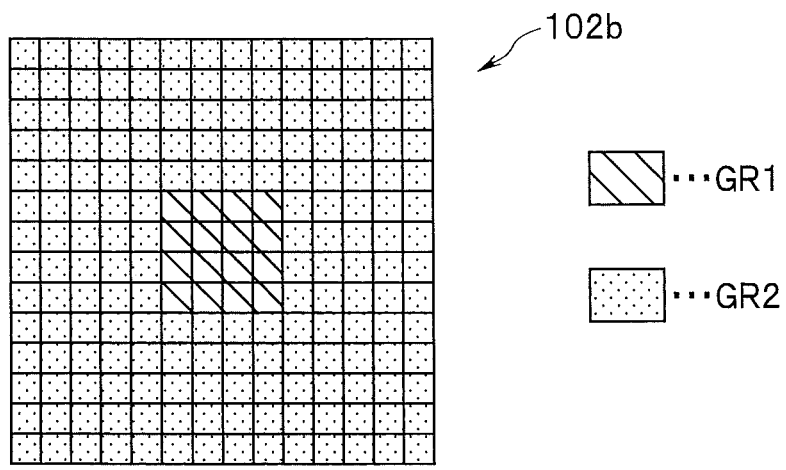
FIG. 9 schematically illustrates how to divide into a group GR1 and a group GR2 in processing related to a calculation of pixel shift correction values.

First, the controller 25 divides the coordinate positions of the respective sampling pixels included in the mapping table MPT1 or MPT2 in the memory 24 into a group GR1 included in the center portion of the region for pixel shift correction 102b and a group GR2 included in a peripheral portion other than the center portion. FIG. 9 schematically illustrates how to divide into the group GR1 and the group GR2 in the processing related to the calculation of pixel shift correction values.

Specifically, when the image size of the region for pixel shift correction 102b is 400×400 pixels, for example, the controller 25 divides the coordinate positions of the respective sampling pixels included in the mapping table MPT1 or MPT2 in the memory 24 into the group GR1 included in a range (region) of 150×150 pixels located at the center portion of the region for pixel shift correction 102b and the group GR2 included in the peripheral portion other than the center portion, as schematically shown in FIG. 9. Such a manner how to divide into the group GR1 and the group GR2 shows one example in the case where the distance between the distal end surface of the insertion portion 11 and the bottom surface portion 102 is a predetermined distance. Therefore, with the present embodiment, the ranges (regions) of the center portion and the peripheral portion of the region for pixel shift correction 102b are preferably set to be ranges (regions) having suitable sizes in accordance with the distance between the distal end surface of the insertion portion 11 and the bottom surface portion 102.

Next, the controller 25 extracts the coordinate positions of the respective sampling pixels constituting the segments in the horizontal direction of the lattice pattern of the region for pixel shift correction 102b from the coordinate positions of the respective sampling pixels which belong to the group GR1 or GR2. Specifically, the controller 25 extracts the part drawn in the second color in the region for pixel shift correction 102b, for example, as the coordinate positions of the respective sampling pixels constituting the segments in the horizontal direction of the lattice pattern of the pixel shift correction region 102b.

Given the case where the coordinate positions of the respective sampling pixels constituting one segment in the horizontal direction of the lattice pattern of the region for pixel shift correction 102b are represented by (xi, yi) (in this regard, 0≤i≤N−1), and a spline curve in the horizontal direction, which is calculated based on the coordinate positions of the respective sampling pixels, is represented by f (xi), an evaluation value σ corresponding to the spline curve f (xi) can be expressed by the following equation (1). In the following equation (1), ωi represents a predetermined constant number, g represents a weighting factor which is a positive value, and $f^{(M)}$ (xi) represents M-th derivative function of the spline curve f (xi).

$$\sigma = \sum_{i=0}^{N-1} \omega i \{f(xi) - yi\}^2 + g \int_a^b \{f^{(M)}(xi)\}^2 dx \quad (1)$$

The first item on the right side of the equation (1) is treated as a scale for measuring to what extent the spline curve f (xi) is separated from the coordinate positions (x0, y0), (x1, y1), ... (x (N−1), y (N−1) of the respective sampling pixels constituting one segment in the horizontal direction of the lattice pattern of the region for pixel shift correction 102b. Therefore, as the value of the first item on the right side of the equation (1) becomes smaller, for example, the separation between the coordinate positions (x0, y0), (x1, y1), ... (x (N−1), y (N−1) of the respective sampling pixels constituting the one segment in the horizontal direction of the lattice pattern of the region for pixel shift correction 102b and the spline curve f (xi) becomes smaller.

In addition, the second item on the right side of the equation (1) is treated as a scale for expressing the magnitude of the fluctuation of the spline curve f (xi). Therefore, as the value except for the weighting factor g in the second item on the right side of the equation (1) becomes smaller, for example, the spline curve f (xi) becomes smoother.

That is, the pixel shift correction values in the vertical direction corresponding to the Y-coordinate values yi can be calculated by calculating the spline curve f (xi) for which the evaluation value σ on the left side of the equation (1) becomes minimum, and by further obtaining a difference between the calculated spline curve f (xi) in the horizontal direction and the Y-coordinate values yi of the sampling pixels (by performing calculation of f(xi)-yi). In addition, with the calculation using the above-described equation (1), for example, the pixel shift correction values in the horizontal direction corresponding to the X-coordinate values can be also calculated by calculating the spline curve in the vertical direction for which the evaluation value 6 on the left side of the equation (1) becomes minimum, and further obtaining a difference between the calculated spline curve in the vertical direction and the X-coordinate values of the sampling pixels.

When scanning is performed (the illumination fibers 12 are swung) in a spiral scanning pattern, the amount of shift of the coordinate positions of the sampling pixels which belong to the group GR1 as the region where the scanning density is the highest is considered to become relatively large in relation to the amount of shift of the coordinate positions of the sampling pixels which belong to the group GR2.

In response to the above-described matter, with the present embodiment, in order to address the occurrence of distortion in the case where the scanning is performed in the spiral scanning pattern, the value of the weighting factor g applied to the equation (1) when calculating the pixel shift correction values of the respective sampling pixels which belong to the group GR1 is set to be larger than the value of the weighting factor g applied to the equation (1) when calculating the pixel shift correction values of the respective sampling pixels which belong to the group GR2, for example, to thereby allow the pixel shift correction values based on the spline curves different from each other to be calculated in the two groups GR1 and GR2.

In other words, with the present embodiment, in order to address the occurrence of distortion in the case where the scanning is performed in the spiral scanning pattern, a first spline curve to be used for calculating the pixel shift correction values of the respective sampling pixels which belong to the group GR1 is calculated with the equation (1) in which the value of the weighting factor g is set so as to place emphasis on the smoothness of the spline curve itself, while a second spline curve to be used for calculating the pixel shift correction values of the respective sampling values which belong to the group GR2 is calculated with the equation (1) in which the value of the weighting factor g is set so as to place emphasis on the low degree of separation of the spline curve with respect to the coordinate positions of the sampling pixels, for example.

The present embodiment enables the spline curves preferable for calculating the pixel shift correction values to be calculated not only for addressing the distortion which occurs in the case where the scanning is performed in the spiral scanning pattern but also for addressing the distortion which occurs in the case where scanning is performed in another scanning pattern, by appropriately changing the setting of the value of the weighting factor g in the equation (1).

In addition, in the present embodiment, for example, the range (region) of the group GR1 may be set to partly overlap the range (region) of the group GR2, to enable a smooth connection of the first spline curve to be used for calculating the pixel shift correction values of the respective sampling pixels which belong to the group GR1 and the second spline curve to be used for calculating the pixel shift correction values of the respective sampling pixels which belong to the group GR2.

Furthermore, with the present embodiment, weighting depending on the distance between the pixels is performed on either the pixel shift correction values calculated in the respective pixels which belong to the group GR1 or the pixel shift correction values calculated in the respective pixels which belong to the group GR2, for example, to enable also the pixel shift correction values in the respective interpolation pixels and in the respective pixels included in the region for white balance adjustment 102a to be calculated.

That is, the above-described calculation is performed in the step S4 in FIG. 8, and thereby the pixel shift correction values in the horizontal direction and the pixel shift correction values in the vertical direction are calculated for the respective pixels included in the same image as the one used for the extraction of the region for pixel shift correction 102b in the step S3 in FIG. 8, and the calculated pixel shift correction values in the horizontal and vertical directions are written into the mapping table MPT1 or MPT2 in the memory 24.

The controller 25 performs the processing in the step S4 in FIG. 8, and then determines whether the pixel shift correction values for the two mapping tables MPT1 and MPT2 are calculated by confirming the information stored in the memory 24 (step S5 in FIG. 8).

When the controller 25 acquires the determination result that the pixel shift correction values have not been calculated for either the mapping table MPT1 or the mapping table MPT2, the controller 25 returns to the step S3 in FIG. 8 to perform the processing in the step S3.

In addition, when the controller 25 acquires the determination result that the pixel shift correction values are calculated for both of the mapping tables MPT1 and MPT2, the controller 25 generates corrected images for two frames which are respectively subjected to the white balance adjustment processing using the white balance correction values stored in the memory 24 and the pixel shift correction processing using the pixel shift correction values written into the mapping tables MPT1 and MPT2 stored in the memory 24 (step S6 in FIG. 8).

After that, the controller 25 determines whether the white balance adjustment processing and the pixel shift correction processing are normally performed on both of the corrected images for two frames which were generated in the step S6 in FIG. 8 (step S7 in FIG. 8).

When the controller 25 acquires the determination result that the white balance adjustment processing and the pixel shift correction processing have not been normally performed on either one of the images for two frames generated in the step S6 in FIG. 8, the controller 25 respectively abandons the white balance correction values stored in the memory 24 and the pixel shift correction values written into the mapping tables MPT1 and MPT2 stored in the memory 24, and then performs the processing from the step S1 in FIG. 8 again.

In addition, when the controller 25 acquires the determination result that the white balance adjustment processing and the pixel shift correction processing have been normally performed on both of the images for two frames generated in the step S6 in FIG. 8, the controller 25 saves in the memory 24 the corrected images for two frames and the endoscope information read from the memory 16 of the scanning endoscope 2 connected to the main body apparatus 3 in association with each other (step S8 in FIG. 8), and then completes a series of processing for acquiring the white balance correction values and the pixel shift correction values.

Specifically, the controller 25 causes the corrected images for two frames generated in the step S6 in FIG. 8 and a GUI (Graphical User Interface) for urging the operator or the like to select whether or not the white balance adjustment processing and the pixel shift correction processing are normally performed to be displayed together on the monitor 4, for example. When the controller 25 detects that a GUI button on which character strings indicating negative such as "NO" are written is depressed by the operator or the like based on the operation of a keyboard or a pointing device (neither not shown) by the operator or the like, for example, the controller 25 acquires the determination result that the white balance adjustment processing and the pixel shift correction processing have not been normally performed on either one of the corrected images for two frames generated in the step S6 in FIG. 8. When the controller 25 detects that a GUI button on which character strings indicating affirmative such as "YES" is written is depressed based on the operation of the keyboard or a pointing device (neither not shown) by the operator or the like, for example, the controller 25 acquires the determination result that the white balance adjustment processing and the pixel shift correction processing are normally performed on both of the corrected images for two frames generated in the step S6 in FIG. 8.

The controller 25 has a function as a determination section, and determines the necessity or unnecessity of the acquisition of the pixel shift correction values with reference to the endoscope information and the corrected images that are saved in association with each other in the memory 24, and executes or omits the processing steps corresponding to the steps S3 to S8 in FIG. 8 based on the determination result.

Specifically, when the controller 25 reads from the memory 16 the same endoscope information as that already saved in the memory 24 and detects that a difference value (a value corresponding to a distortion amount or a pixel shift amount) between the corrected images stored in association with the endoscope information and the images before correction which were generated based on the sampling pixels and the interpolation pixels before performing the processing in the step S1 in FIG. 8 is equal to or smaller than a predetermined threshold, for example, the controller 25 operates so as to determine that the acquisition of the pixel shift correction value is unnecessary and then omit the processing steps corresponding to the steps S3 to S8 in FIG. 8 based on the determination result.

On the other hand, when the controller 25 reads from the memory 16 the same endoscope information as that already saved in the memory 24, and detects that the difference value (the value corresponding to the distortion amount or the pixel shift amount) between the corrected images stored in association with the endoscope information and the images before correction which were generated based on the sampling pixels and the interpolation pixels before performing the processing in the step S1 in FIG. 8 is larger than a predetermined threshold, for example, the controller 25 operates so as to determine that the acquisition of the pixel shift correction values is necessary and then execute the processing steps corresponding to the steps S3 to S8 in FIG. 8 based on the determination result.

As described above, the present embodiment enables the white balance correction values and the pixel shift correction values in the images can be collectively acquired, based on the images acquired by scanning the region for white balance adjustment 102a and the region for pixel shift correction 102b of the test chart device 101. Therefore, the present embodiment enables the amount of operation required for observation using the scanning endoscope to be reduced.

In addition, as described above, with the present embodiment, the controller 25 is configured to determine the necessity or unnecessity of the acquisition of the pixel shift correction values in the scanning endoscope 2 which has been connected to the main body apparatus 3 in the past. Therefore, the present embodiment enables a part of operations performed before the observation using the scanning endoscope to be omitted, i.e., there is no need for the operator to visually check the images to determine the necessity or unnecessity of the acquisition of the pixel shift correction values, every time when the scanning endoscope 2 is connected to the main body apparatus 3. As a result, the amount of work required for observation using the scanning endoscope can be reduced.

In the present embodiment, when the pixel values of respective color components are indicated with the values from 0 to 255 (eight bits), a series of processing steps in FIG. 8 may be performed by previously eliminating the pixels whose pixel values of the R component, G component, and B component are all 255, for example.

The present invention is not limited to the above-described embodiment, and it is needless to say that various changes and modifications are possible without departing from the gist of the invention.

What is claimed is:

1. A scanning endoscope system comprising:
 a scanning endoscope including: a light-guiding section that guides illumination light emitted from a light source; a driving section that enables the light-guiding section to swing such that an irradiation position of the illumination light emitted to an object through the light-guiding section draws a trajectory corresponding to a predetermined scanning pattern; and a light-receiving section that receives return light of the illumination light emitted to the object;
 a test chart device comprising a plane portion including a first region and a second region;
 a light detection section configured to generate a signal corresponding to an intensity of the return light received at the light-receiving section and output the generated signal;
 a pixel generation section configured to generate sampling pixels on the predetermined scanning pattern by sampling the signal outputted from the light detection section in a given sampling cycle;
 a first correction value calculation section configured to extract the first region from an image of the plane portion which includes the respective sampling pixels generated by the pixel generation section, and to further calculate a first correction value to be used for color balance adjustment of an image of the object based on a pixel value of each of the sampling pixels included in the first region; and
 a second correction value calculation section configured to extract the second region from the image of the plane portion which includes the respective sampling pixels generated by the pixel generation section, and to further calculate a second correction value to be used for pixel shift correction of the image of the object based on a pixel position of each of the sampling pixels included in the second region.

2. The scanning endoscope system according to claim 1, wherein the test chart device includes the first region provided at a peripheral portion of the plane portion and the second region provided at the center portion of the plane portion.

3. The scanning endoscope system according to claim 1, wherein
 the illumination light is white light obtained by mixing light of three colors of red, green, and blue, and
 the second region in the plane portion includes a lattice pattern composed of segments in a vertical direction respectively drawn in a first color of the three colors and segments in a horizontal direction respectively drawn in a second color of the three colors, the second color being different from the first color.

4. The scanning endoscope system according to claim 1, wherein the second correction value calculation section calculates the second correction value by applying a first calculation method to the pixel position of each of the sampling pixels included in the center portion of the second region, and calculates the second correction value by applying a second calculation method different from the first calculation method to the pixel position of each of the sampling pixels included in the peripheral portion of the second region.

5. The scanning endoscope system according to claim 1, further comprising:
   a storage section configured to be able to save a corrected image of the plane portion obtained by respectively applying the first correction value and the second correction value to the image of the plane portion which includes the respective sampling pixels generated by the pixel generation section; and
   a determination section that determines necessity or unnecessity of calculation of the second correction value by the second correction value calculation section, based on the corrected image of the plane portion saved in the storage section and the image before correction of the plane portion, the image before correction including the respective sampling pixels generated by the pixel generation section.

6. The scanning endoscope system according to claim 1, wherein the predetermined scanning pattern is a spiral scanning pattern.

7. The scanning endoscope system according to claim 1, wherein the test chart device is formed as a bottomed cylinder body having an internal space into which a distal end portion of the scanning endoscope is insertable, and includes the plane portion at a bottom surface portion inside the bottomed cylinder body.

* * * * *